United States Patent [19]

Hasegawa et al.

[11] Patent Number: 5,123,413
[45] Date of Patent: Jun. 23, 1992

[54] ELECTRIC THERAPEUTIC APPARATUS

[75] Inventors: Ryozo Hasegawa, Tokyo; Kazutoshi Mizoi, Watarai; Akira Kato, Iwakuni; Toshimi Nishiyama, Koganei, all of Japan

[73] Assignee: Teijin Limited, Osaka, Japan

[21] Appl. No.: 605,938

[22] Filed: Oct. 30, 1990

Related U.S. Application Data

[62] Division of Ser. No. 163,513, Mar. 2, 1988, abandoned.

[30] Foreign Application Priority Data

| May 27, 1987 | [JP] | Japan | 62-128473 |
| Nov. 26, 1987 | [JP] | Japan | 62-296125 |
| Dec. 17, 1987 | [JP] | Japan | 62-317444 |

[51] Int. Cl.$^5$ .................. A61N 1/32; A61N 1/04
[52] U.S. Cl. .................. 128/419 G; 128/420 A; 128/802; 128/803
[58] Field of Search ........... 128/419 G, 420 A, 422, 128/644, 791, 793, 802, 803

[56] References Cited

U.S. PATENT DOCUMENTS

| 768,721 | 8/1904 | Bassell | 128/793 |
| 1,652,804 | 12/1927 | Wappler | 128/802 |
| 2,549,836 | 4/1951 | McIntyre et al. | 128/644 |
| 2,622,601 | 12/1952 | Nemes | 128/422 |
| 3,659,614 | 5/1972 | Jankelson | 128/791 |
| 3,774,620 | 11/1973 | Hansjurgen | 120/420 A |
| 3,958,577 | 5/1976 | Rodler | 128/420 A |
| 4,071,033 | 1/1978 | Nawracaj et al. | 128/420 A |
| 4,770,180 | 9/1988 | Schmidt et al. | 128/644 |

FOREIGN PATENT DOCUMENTS

| 228048 | 8/1909 | Fed. Rep. of Germany . |
| 259658 | 6/1912 | Fed. Rep. of Germany . |
| 2658096 | 12/1977 | Fed. Rep. of Germany . |
| 3207050 | 9/1983 | Fed. Rep. of Germany . |
| 1130680 | 10/1956 | France | 128/420 A |
| 2342082 | 9/1971 | France . |
| 2493154 | 5/1982 | France | 128/419 G |
| 60-31766 | 2/1985 | Japan . |
| 2129308 | 5/1984 | United Kingdom | 128/422 |

OTHER PUBLICATIONS

Kawai, Sputum and Expectoration (Drug and Other therapy) J. Jpn Bronchoesophgal. Soc. vol. 35, No. 2, 1984.
Studies on Electric Properties of Interference Low Frequency and Its Safety on Living Body, Therapeutic Research, vol. 3, No. 1, 1985.
Shuts et al., "ILF Therapy on Patients with Bronchecl Asthma", Allergy 35(12), 1986.

Primary Examiner—Lee S. Cohen
Attorney, Agent, or Firm—Kenyon & Kenyon

[57] ABSTRACT

An electric therapeutic apparatus for inducing an expectoration of sputum by a patient having difficulty therewith by using an interference low frequency wave, which comprises at least one electric current generating unit for generating an electric current having an intermediate frequency, an electric current detecting unit for detecting an electric current when an electric power is supplied, an electric current controlling unit for controlling the current flowing in the apparatus when an electric power is supplied, and at least one pair of electrodes adapted to be attached to a human body, the input of which is connected to the current generating unit. The apparatus can be combined with a separate bioelectric potential measuring unit with a suitable coupling means so that the electric therapeutic treatment can be carried out while checking the bioelectric potential; this unit being, for example, an electrocardiogram, and therefore, if an abnormal bioelectric potential is detected during the electric therapeutic treatment, the current supplied to the therapeutic apparatus is stopped or reduced so that a treatment having a high safety and excellent accuracy can be obtained. Moreover, a fixing device of an electrode in which a plurality of electrodes can be easily fixed to any portion of a human body is provided.

10 Claims, 12 Drawing Sheets (CHEST)  (BACK)

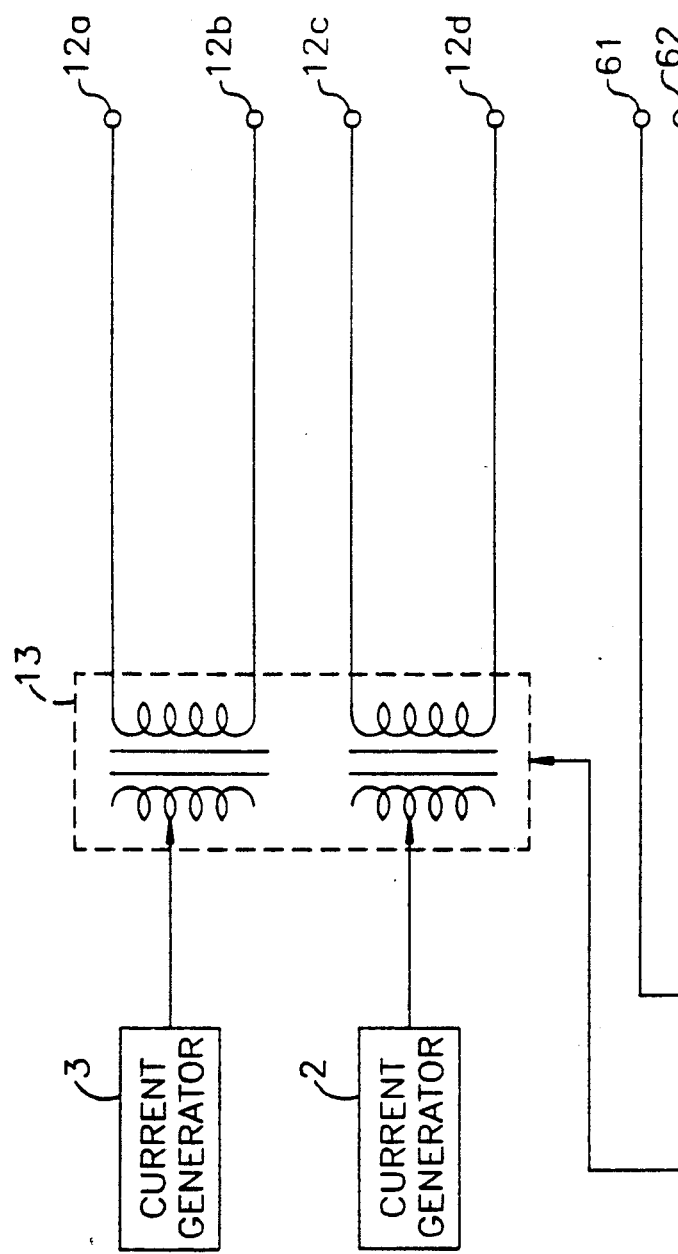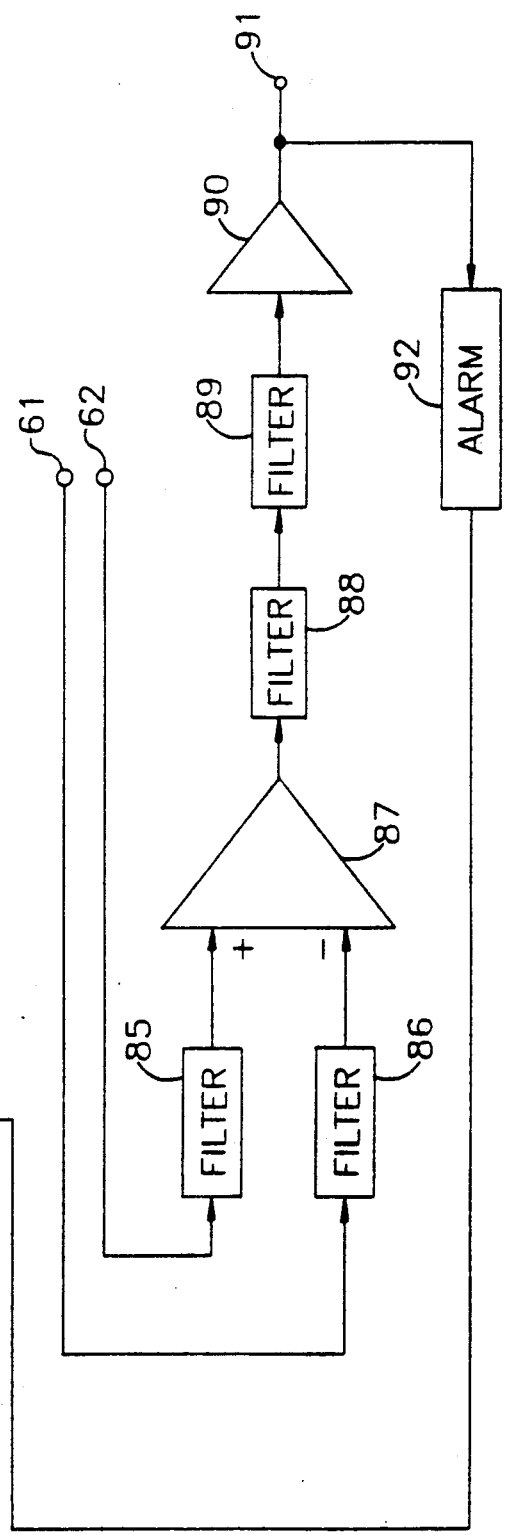
FIG. 7

ELECTRIC THERAPEUTIC APPARATUS

This is a division of application Ser. No. 163,513, filed Mar. 2, 1988, now abandoned.

BACKGROUND OF THE INVENTION

1. Field of the Invention

The invention relates to a therapeutic apparatus for the support of patients having difficulty in sputum expectoration when afflicted with a respiratory disease such as chronic bronchitis, bronchiolitis, bronchial asthma, bronchiectasis, pulmonary tuberculosis, and pulmonary emphysema. More particularly, the invention relates to a therapeutic apparatus using an interference low frequency wave, which enables sputum in the trachea and a bronchial tube of the chest to be easily expectorated by supplying an electrical stimulation.

2. Description of the Related Arts

Recently, due to the increase in the population and an increase in the number of aged people, and further, changes in environmental conditions, for example, air pollution, the number of people suffering from chronic respiratory diseases such as chronic bronchitis, bronchial asthma and pulmonary emphysema has increased.

Among the symptoms, such as sputum accumulation, coughing, and difficulty in breathing which are accompanied by such respiratory diseases, the difficulty of expectoration of sputum appears most frequently in medical records and has becomes one of the main symptoms particularly in the pneumonopathy of a chronic obstruction, for example, chronic bronchitis, bronchial asthma and pulmonary emphysema as well as the labored respiration.

In the medical treatment of respiratory diseases, it is very important to cause the expectoration of sputum, which is a major cause of labored respiration and of infections of, for example, a respiration tract, and such expectoration is effected by a drug treatment and physiotherapy.

Known pharmaceutical compounds for effecting expectoration in a drug treatment are, for example, iodic salt, benzylamine, ferment compound, cysteine compound, and "ALEVAIRE".

All of these compounds for enabling expectoration directly or indirectly affect a rheological characteristic such as an adhesive power, a spinnability or a phenomena of thixotropy of a sputum. However, inevitably side-effects occur depending upon the usage of such compounds, and therefore often such a treatment will have an adverse effect on the human body. Also, in many experimental medical treatments, a sufficient expectoration was not obtained when these compounds were used.

In this connection, physiotherapy by a postural drainage method is well known.

In this method, the patient's whole body or the chest portion must be inclined to enable sputum to be expectorated under the force of gravity, and in addition, a method of tapping the chest or applying external vibration to the chest is used to enable the sputum to be easily expectorated.

Nevertheless, although there is less fear of side-effects from the drug treatment, it has a defect in that the expectoration of sputum is not altogether satisfactory.

In another method for stimulating expectoration, as one kind of physiotherapy a pressure wave having a frequency of less than 10 Hz is directly supplied into the trachea and a respiratory tract by way of the trans-tracheal, but this method requires many improvements.

As a new treatment for effecting expectoration in physiotherapy, a treatment using a therapeutic apparatus for improving a respiratory function and/or symptoms thereof by utilizing a low frequency wave is disclosed in, for example, Japanese Unexamined Patent Publication 60-31766, but the effecting of expectoration by electric stimulation with a interference low frequency wave varies greatly, depending upon the conditions under which the electric stimulation is carried out and the position at which the therapy is applied.

Therefore, much research has been made into the conditions needed to obtain the best effects from this kind of treatment.

SUMMARY OF THE INVENTION

The object of this invention is to provide an electric therapeutic apparatus and method for supporting patients having difficulty in effecting an expectoration of sputum, because of a respiratory disease, in a more reliable and safe manner.

Another object of this invention is to provide an electric therapeutic apparatus in which an electric therapeutic device is coupled with a device for detecting a bioelectric potential, in order to perform such a therapeutic treatment in the safest manner by checking the condition of a patient during the treatment.

A further object of the invention is to provide a device to be used with the therapeutic apparatus, by which device the electrodes can be easily applied to a human body.

BRIEF DESCRIPTION OF THE DRAWINGS

FIG. 6 and FIG. 7 are block diagrams of another embodiment of a therapeutic apparatus of this invention in which a bioelectric potential measuring means is incorporated;

DESCRIPTION OF THE PREFERRED EMBODIMENTS

To attain the object of the invention, the electric therapeutic apparatus basically comprises at least one electric current generating means for generating an electric current having an intermediate frequency, an electric current detecting means for detecting an electric current when an electric power is supplied, an electric current controlling means for at least controlling the current in such a way that a current of at least 6 mA flows in the apparatus when an electric power is supplied, and at least one pair of electrode means consisting of at least two electrodes which is adapted to be attached to a portion of a human body to be treated, and two conductive lines having an input thereof connected to the output of the electric current generating means. The preferred embodiment of the electric therapeutic apparatus of this invention will be now described with reference to the accompanying drawings.

Figure 1:
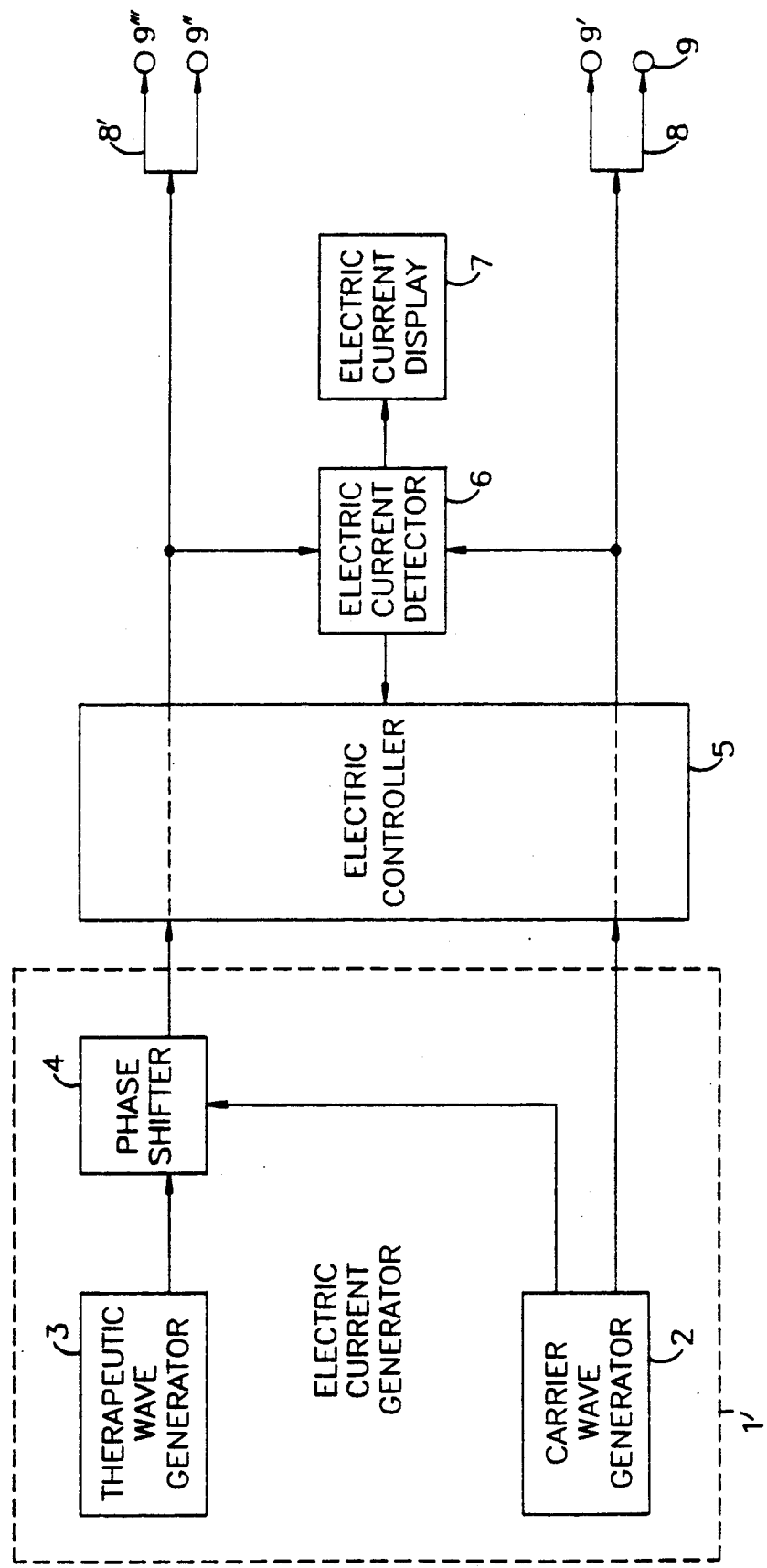
FIG. 1 is a block diagram of one embodiment of a therapeutic apparatus of this invention.

FIG. 1 is a block diagram of one example of this invention.

FIG. 1 shows an apparatus having two electric current generating means and two pairs of electrodes means, but in this invention, an apparatus having one electric current generating means and one pair of electrode means also can be applied.

When the latter apparatus is used, an electric current having a single pulse wave, for example, a spiked pulse wave with a low frequency, is used for the therapy and the electric circuit for this kind of therapeutic apparatus is much simpler than that shown in FIG. 1. Hereinafter, the explanation of this invention will be based substantially on the apparatus shown in FIG. 1. In FIG. 1, the electric current generating means 1 comprises a carrier wave generating device 2, a therapeutic wave generating device 3, and a phase shifter 4.

Note, in another embodiment of this invention, the apparatus may comprise two separate carrier wave generators generating carrier waves each having a different frequency, as the electric current generating means. In this case, such a generator is used as the therapeutic wave generator 3. In this invention, the term an intermediate frequency refers to an electromagnetic wave preferably having a frequency of 1000 Hz to 10,000 Hz, more specifically 3000 Hz to 5000 Hz, in practical usage. Generally speaking, a frequency of an electric current used for the therapy is preferably much higher than the frequency of a bioelectric potential of a portion to be detected.

Further, an electric current having a frequency of about 4000 Hz is preferably used, because when such an electric current is used, since the electric impedance of a skin of a human body is generally low, the electric current can easily flow through the human body and a threshold value of an electric shock (macroshock) to a human body is much higher than that of a commercial current having a frequency of 50 Hz or 60 Hz, for example, as used in Japan, and thus provides a greater safety.

In this embodiment in FIG. 1, contrary to the case of using the one electric current generating means, an interference low frequency wave is used for the therapy which is generated inside of a human body by two electric currents, each having a different frequency, emitted from each electrode connected to the separate electric current generating means.

In this embodiment, a frequency of the interference low frequency wave used as a therapeutic frequency is preferably from 30 Hz to 150 Hz. In this case, for example, one carrier wave having a frequency of 4000 Hz may be generated from a carrier wave generating device 2, and another carrier wave having a frequency of 4100 Hz may be generated from a phase shifter 4 connected to the carrier wave generating device 2. In another method, two currents each having a different frequency may be generated from the generators 2 and 3, respectively, without using the phase shifter 4. Each carrier wave thus generated is then output from two electrodes 9, 9' or 9", 9''' of the respective electrode means 8 and 8', and the electric therapy is performed with four electrodes 9, 9', 9" and 9'''.

As shown in FIG. 1, the apparatus further comprises an electric current detecting means 6 for detecting the current flowing to the two pairs of electrode 9, 9' and 9", 9''', an electric current display means 7 for displaying the current detected by the detecting means 6, and a controlling means 5 including an electric current controlling means and a time setting means for setting a time for supplying the electric current to the apparatus.

As an electric current controlling means, a means for changing an amplification degree of an amplifier or a means for changing a resistance value of a resister may be used, for example.

Figure 2:
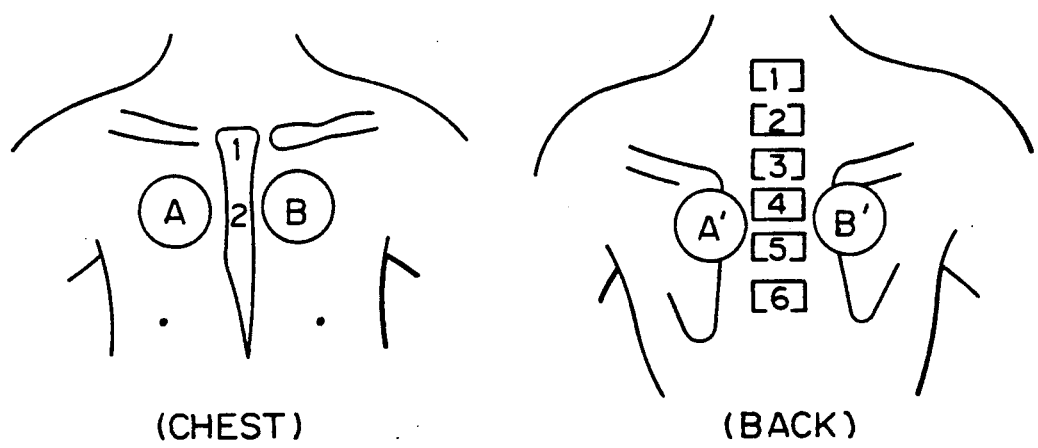
FIG. 2 show positions at which an electrode is attached to a human body in this invention.

As shown in FIG. 2, when the electrodes are applied to a human body for the therapy, two electrodes for the chest portion and another two electrodes for the back portion are arranged in such a way that the pair of the electrodes A—A' and the pair of the electrodes B—B' are intercrossed to generate a interference low frequency wave having a frequency of 100 Hz at the cross point thereof in a human body.

A remarkable effect of causing expectoration can be obtained with the electric stimulation provided by this interference low frequency wave.

The reason for this was determined from the results of animal experiments, whereby it was found that an electric stimulation of the interference low frequency wave first exasperates a secretion of a respiratory tract fluid, and thus a rheological characteristic of the sputum per se is changed to a characteristic whereby an easy flowability of the sputum is obtained, and in addition; the mucociliary transportation effect is increased, and therefore an expectoration of sputum can be obtained.

Accordingly, it was then determined how to apply this expectoration function obtained by animal experiments to a human body, from the viewpoints of the beneficial and adverse effects to be expected.

According to results of a clinical test, described hereunder, on the expectoration of sputum, the frequency of the interference low frequency wave is preferably in a range of from 30 Hz to 150 Hz. When a frequency of less than 30 Hz was applied, the stimulation was too strong and often the patients felt discomfort.

On the other hand, when a frequency of more than 150 Hz was applied, the effect was reduced. Accordingly, preferably the frequency is 50–100 Hz.

In addition to the frequency of the interference low frequency wave, an amount of electric current used is another important factor in the therapy of this invention, and should be made a suitable value for obtaining a desirable effect.

In accordance with another clinical experiment, it was found that, when an electric current of less than 3 mA was supplied to the apparatus for the therapy, little electrical stimulation was felt by the patients and when a current of less than 5 mA was supplied, it was difficult to induce the expectoration. Therefore, a current of more than 6 mA is required as a lower limit of the electric current to be used for the therapy.

On the other hand, with regard to an upper limit of the electric current used for the therapy, the effect on a human body caused by the electric stimulation gives more discomfort in relation to the extent of the effect of inducing expectoration. For example, when a current of more than 50 mA is applied to a human body, the considerably strong electric stimulation felt caused twitching of the muscles of the human body, and therefore, the use of a current of more than 50 mA is not preferable because of the discomfort this causes patients.

The upper limit of this current can not be simply determined, because of individual differences, and thus it is better to set the value of the upper limit for each patient to ensure the safety of a patient using this therapeutic apparatus.

From a viewpoint of safety, when using a therapeutic apparatus for inducing an expectoration, preferably the upper limit of the current to be supplied is previously set, and when the instant amount of the current exceeds the upper limit, the amount of the current should be automatically reduced by a current controlling means such as an amplifier provided in the controlling means 5 as shown in FIG. 1, or the supply of the current cut off by using, for example, an over current prevention means which may be added to the control means 5 shown in FIG. 1.

Further, it is more beneficial in practice to provide a setting device for setting the upper limit of an amount of current supplied, in accordance with the characteristics of the patient undergoing this therapy.

The period for which the electric current is supplied for the therapy should be within the range of from 5 minutes to 30 minutes.

It is assumed that the electric stimulation of the interference low frequency wave induces the expectoration through parasympathetic nerves, for the above reason, and it is known from clinical examinations that the effect thereof continues for about from several hours to several tens of hours from the time the therapy is performed. Therefore, the therapy period is preferably within a range of from 10 minutes to 20 minutes, as a time for which such electric stimulation can be safely accepted by a human body.

As shown in FIG. 2, when two carrier waves each having a different frequency, for example, 4000 Hz and 4100 Hz, are supplied for the therapy and are emitted from the electrodes in such a way that one carrier wave is emitted from a pair of electrodes positioned on the left chest portion and right back portion (B—B' in FIG. 2) and another is emitted from another pair of electrodes positioned on the right chest portion and left back portion (A—A' in FIG. 2), an interference low frequency wave having a frequency of 100 Hz is generated, and the resultant electric stimulation has a good effect of inducing expectoration.

In this invention, the electrode means comprises an input line for receiving an electric current from the current generating means and at least two conductive lines connecting the input line and the electrode, wherein at least two electrodes are connected to each end of the conductive line, which electrodes can supply the necessary current and can be attached to any portion of a human body. As the electrodes, any type of the electrode described later can be used in this invention.

As explained above, it is necessary to ensure the safety of such a therapeutic treatment for inducing expectoration, because of the possibility that twitching of a muscle of a human body may occur if the amount of electric current used in the therapy is too high, depending upon the individual patient.

Further, it is necessary to ensure the safety of all electric therapeutic apparatuses other than the therapeutic apparatus for inducing expectoration by using an interference low frequency wave, to give the patients using such an apparatus a feeling of safety, and therefore, enable the patients to receive the therapeutic treatment in a relaxed condition.

Therefore, in this invention, another type of therapeutic apparatus in which a bioelectric potential measuring means is attached to the therapeutic apparatus is provided. More precisely, in this therapeutic apparatus, a bioelectric potential measuring means is coupled with the apparatus in such a way that a part of the electrode means for supplying the electric current for therapy is simultaneously used as at least a part of the electrodes of the bioelectric potential measuring means as an input terminal, or a part of an output terminal of the bioelectric potential measuring means is connected to the controlling means of the apparatus.

According to this embodiment, as the apparatus has a bioelectric potential detecting means incorporated therein, the therapeutic treatment and the measurement of the bioelectric potential of a human body can be carried out simultaneously, and therefore, the safety of such an apparatus is increased.

According to one embodiment of the invention, the electric therapeutic apparatus comprises at least one electric current generating means for generating an electric current having an intermediate frequency, an electric current detecting means for detecting an electric current when an electric power is supplied to the apparatus, an electric current controlling means for controlling the current flowing in the apparatus when an electric power is supplied, at least one pair of electrode means consisting of at least two electrodes which is adapted to be attached to a portion of a human body to be treated, and two conductive lines, an input thereof being connected to the output of the electric current generating means, and a capacitive coupling means provided on each conductive line in the electrode means. A bioelectric potential measuring means is further provided and at least one line selected from an output line means and input line mean thereof is connected to the line connected between the electric current generating means and the electrode means.

The characteristic feature of this invention is, as mentioned above, that at least a part of the electrode of an electrode means for supplying an electric cyclic current used for the therapeutic treatment is commonly used as a part of the electrode for the bioelectric potential measuring means, and the common use of the electrode can be performed by providing a capacitive coupling means on at least one conductive line of the electrode means between the electric current generating means for the therapeutic treatment and the electrode for supplying the electric current directly or indirectly to a human body or the electrode per se, to eliminate any substantial loss of the stimulating electric current from the therapeutic treatment and to prevent a bypass of an electric current representing an electrical phenomena over a human body.

Thus, in this invention, a capacitive coupling means is provided on the electrode means especially on a conductive line, for the therapeutic treatment including the electrodes for the therapeutic treatment, and an input line means of the bioelectric potential measuring means is connected to a point between the capacitive coupling means and the electrode.

The number of capacitive coupling means used in this invention depends on the type of therapeutic apparatus, and therefore, if the apparatus has two electrode means each having two electrodes, then at most four capacitive coupling means are required.

The electrode means comprises at least two conductive lines, one end of both lines being connected to an electric current generating means and the other end thereof being provided with an electrode.

As a capacitive coupling means, any type of coupling means which permits a measurement of a bioelectric potential and a supply of electric current for the therapeutic treatment simultaneously, by using a common electrode, can be used in this invention. For example, a condenser may be used as the capacitor.

In the construction of the capacitive coupling means of this invention, a flat plate type capacitor and a cylindrical type capacitor are well known, and further, a fixed capacitor in which an electrostatic capacity is constant and a variable capacitor in which an electrostatic capacity is varied are known. In general, the fixed condenser is used, but a variable condenser in which the electrostatic capacity can be set by an external control may be used.

The materials used for the capacitive coupling means and the configuration thereof are not specifically restricted.

For example, when an electric therapeutic apparatus utilizing an interference low frequency wave caused by two carrier currents each having a different intermediate frequency as a therapeutic electric current and having the same function as that of an electrocardiogram or the like, is used, a capacitive coupling means having an electrostatic capacity showing a considerably low impedance to a carrier current (i.e., conductive reactance) and showing a high reactance to a bioelectric potential based upon an electromotive force caused by the activity of a heart muscle, is preferably used.

When the electric therapeutic apparatus of this invention has at least two electrodes means the capacitive coupling means may be provided on at least one conductive line of the at least two electrode means, having an electrode which is commonly used as the electrode of a bioelectric potential measuring means, but may be provided on another conductive line or another electrode means for reducing an effect caused by a leak current flowing through a human body, if necessary.

The location of the capacitive coupling means may be practically provided on a conductive line of the electrode means for therapeutic treatment, but may be also provided in the electrode per se.

In the latter case, as one example, a conductive plate is used (for example, a metal plate) of a secondary side of the capacitive coupling means as a conductive plate for an electrode, and as another example, a capacitive coupling means is provided by using a dielectric material on a portion of an electrode per se which is used in a capacitively coupled condition with a human body with a dielectric material.

In this invention, the secondary side means a point between the capacitive coupling means and the electrode, and is preferably on a conductive line of the electrode means or a conductive material consisting of a portion of the capacitive coupling means located opposite to the electric current generating means.

An example of this invention is now explained with reference to FIG. 4.

Figure 4:
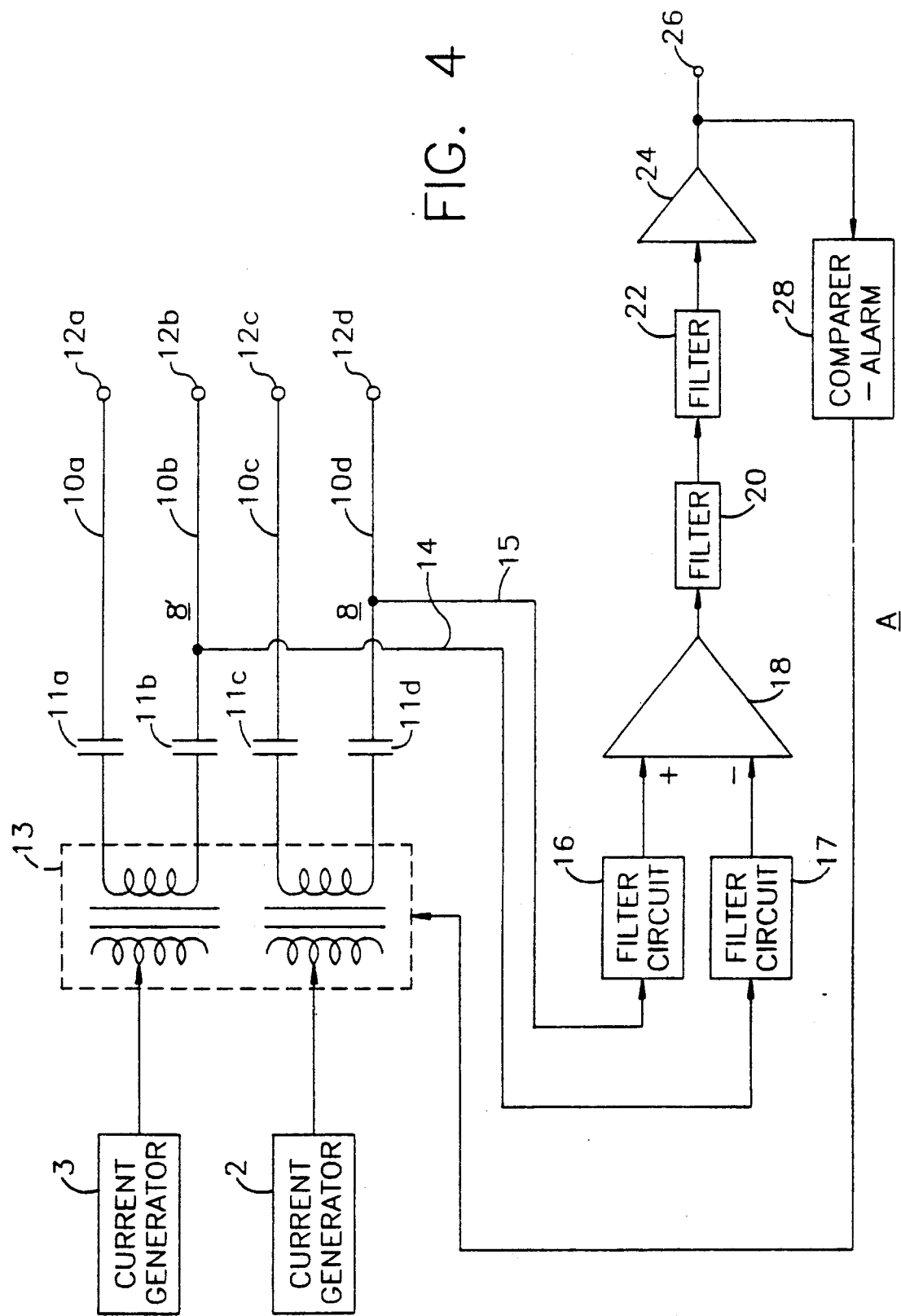
FIG. 4 and FIG. 5 are block diagrams of another embodiment of a therapeutic apparatus in this invention in which a bioelectric potential measuring means is incorporated.

FIG. 4 shows an electric therapeutic apparatus utilizing an interference low frequency wave having two pairs of electrode means, each electrode means consisting of two conductive lines and two electrodes.

Capacitive coupling means $11a$, $11b$, $11c$ and $11d$ are provided on each conductive line means $10a$, $10b$, $10c$ and $10d$ of the two pairs of electrode means 8, 8' for therapeutic treatment and two of each input line means 14, 15 of a bioelectric potential measuring means A are connected respectively to a point at the secondary side of at least one of the capacitive coupling means $11b$ and $11d$ of the respective electrode means and on the conductive lines $10b$ and $10d$ respectively.

This kind of apparatus is preferable for practical use because of the effect of a reduction of the electric current used for the therapeutic treatment to the bioelectric potential measuring means.

A bioelectric potential measuring means of this invention includes a means for taking an electrocardiogram, for example.

Further, in this invention, the electric therapeutic apparatus is characterized in that a bioelectric potential measuring means is provided with a filter circuit 16, 17 on each input line means for filtering a frequency caused by a cyclic current for the therapeutic treatment, and moreover, is provided with a differential amplifier means 18 having input terminals connected to the input line means through the filter means.

The combination of the filter circuit and the differential amplifier means is desirable in practical use for increasing the accuracy of the measurement.

For example, in an electric therapeutic apparatus utilizing an interference low frequency wave as described above, the electric potential caused by an electrical phenomena over a human body is extremely small, compared with a potential caused by an electric carrier wave for the therapeutic treatment; for example, the latter usually has a peak of 4 kHz and a voltage of 10 to 40 volts, and the former has a voltage of from one ten-thousandth to one hundred-thousandth that of the latter.

Accordingly, the use of the filter circuit in this invention is very effective for detecting only a bioelectric potential in the electric current including both electric potentials, by substantially filtering the electric carrier wave for the therapeutic treatment.

A filter circuit of this invention preferably comprises a notch filter ($-60$ dB) having a peak of 4 kHz and a high cut filter having a cutting frequency of 100 Hz ($-24$ dB/oct), to cut off most of the carrier wave.

As described above, in this invention, it is desirable to use a band pass filter for filtering the frequency of the cyclic current for the therapeutic treatment or a high cut filter which does not cut off a frequency caused by a bioelectric phenomena but only cuts off a frequency of a cyclic current for the therapeutic treatment in a single form or in a combination thereof, reducing it by a filter having a high attenuation factor, to increase a function for filtering a frequency other than the frequency caused by a bioelectric potential as much as possible before amplification.

After that, the currents thus passed through the filter circuit for filtering a frequency of a cyclic current for the therapeutic treatment are input to the input terminals of a differential amplifier through respective conductive lines, and thus a residual component of the frequency for the therapeutic treatment is further filtered by increasing a common mode discrimination ratio to, for example, about 80 dB, and accordingly, the measurement of the bioelectric phenomena when, for example, taking an electrocardiogram, can be performed more stably and more accurately.

A bioelectric potential measuring means of this invention includes at least one measuring method selected from a measurement of an electrocardiogram, an electromyogram and an electroencephalogram or the like, but a measurement of an electrocardiogram is the most suitable for this bioelectric potential measuring means.

The bioelectric potential used in this invention is usually detected on a surface of a human body. For example, when the electric therapeutic apparatus utilizing an interference low frequency wave is used to induce an expectation by a patient having a respiratory disease, it is very effective to use a measurement of an electrocardiogram for observing the movement of the heart of the patient simultaneously with the therapeutical treatment, because many patients suffering from this kind of disease usually have heart trouble as a further complication.

In this case, the observation of the condition of the heart of the patient may be carried out either by checking the results of the measurement of an electrocardiogram directly by projection onto a Braun Tube, by output as a hard copy, or by checking a pulse caused by a sharp wave i.e., a spike wave, included in a wave of the electrocardiogram as a signal source and denoting a trigger signal.

Therefore, an electric circuit in which, when an abnormal electrical signal is detected upon a malfunction of the heart, for example, an abnormal heart beat is detected, the supply of the electric current for the therapeutic treatment is reduced or stopped, may be incorporated in this apparatus to further increase the safety of this apparatus.

Especially, when the bioelectric potential measuring means can measure a number of an ictus cordis (heart beat), preferably a comparator is provided for comparing the number of the ictus cordis detected with a range of a normal number of the ictus cordis which can be set by an external input means previously, and further, to provide an abnormal signal generating means for outputting a signal to stop or to reduce the supply of a current for the therapeutic treatment when the number of an ictus cordis detected is higher than normal.

Further, a relay circuit or switching circuit, for example, can be used as a means for stopping or reducing a current for the therapeutic treatment in accordance with such an abnormal signal, and this means may be generally provided in any one of the controlling means, the electric current generating means, and the electrode means, and further, a part thereof may be provided in the bioelectric potential measuring means.

Although an electric therapeutic apparatus in corporating a bioelectric potential measuring means can prevent a supply of an electric current even when an electrode for the therapeutic treatment is not fully in contact with a certain source, the normal measuring operation of a bioelectric potential is stopped, and thus the supply of an electric current to the therapeutic treatment is cut off.

As shown in FIG. 4, electric current generating means 2 and 3 for generating carrier waves having a frequency of 4000 Hz and 4070 Hz, respectively, are provided and a transformer for controlling an output 13 is also provided, and in this embodiment, the electric current generating means for the therapeutic treatment comprises the same means as mentioned above.

Also, conductive lines 10a, 10b, 10c, and 10d for supplying an electric carrier current for the therapeutic treatment, and electrodes 12a, 12b, 12c, and 12d are provided together with the condensers 11a, 11b, 11c and 11d as a capacitive coupling means.

On the other hand, the input lines 14 and 15 as the measuring means of an electrocardiogram are provided and the band pass filters 16 and 17 for filtering almost all of the carrier wave for the therapeutic treatment are also provided.

Moreover, the bioelectric potential measuring means of this invention further comprises a differential amplifier 18 for filtering an in-phase portion of a potential, a high cut filter 20 for cutting off a residual carrier wave, a band pass filter 22 for filtering a commercial cyclic current, and an amplifier 24.

An output terminal 26 of an electrocardiogram is connected to a display means (not shown) and a comparing and alarm generating means 28 for comparing the detected number of an ictus cordis with the predetermined number of an ictus cordis set by an external input means (not shown) and for generating an alarm when the detected number of an ictus cordis falls outside of such a predetermined range or an irregular pulse is detected, is also provided.

Further, a buffer for controlling an impedance (not shown) may be provided between the band pass filters 16 or 17 and the differential amplifier 18, or between the high cut filter 20 and the band pass filter 22.

Figure 5:
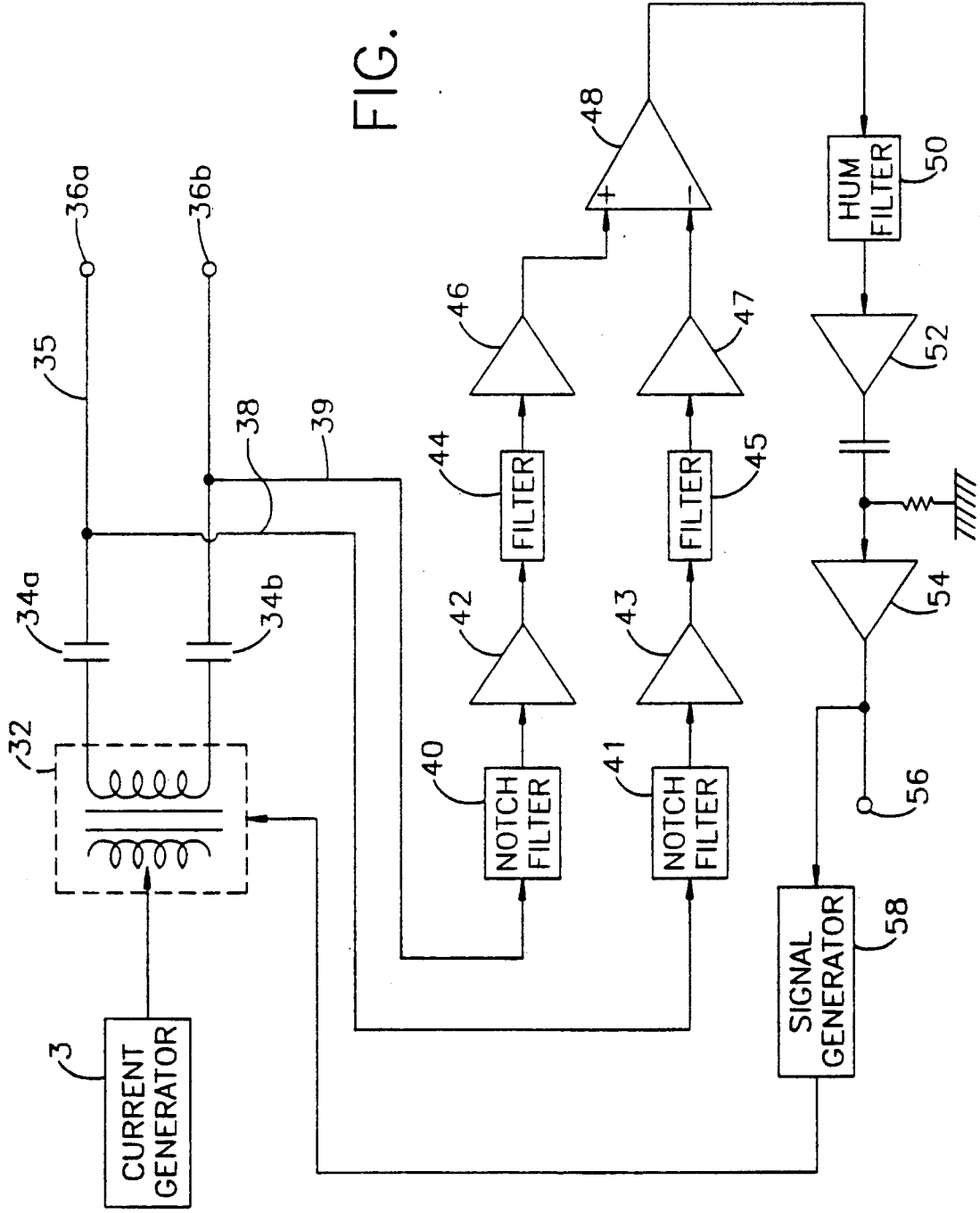

FIG. 5 shows another embodiment of this invention, which comprises only one electric cyclic current generating means 3, a transformer for controlling the output 32, condensers 34a and 34b, a conductive line 35, electrodes 36a and 36b, and further, comprises conductive lines 38 and 39 for measuring a bioelectric potential, T-type notch filters 40 and 41 for filtering a cyclic current for the therapeutic treatment, buffer amplifiers 42 and 43 for matching an impedance on the line, low pass filters 44 and 45 for cutting off a residual frequency of a cyclic current for the therapeutic treatment, buffer amplifiers 46 and 47, a differential amplifier 48 for filtering an in phase portion of a potential, a hum filter 50 for filtering a commercial cyclic current, a buffer amplifier 52, and an amplifier 54.

Also, an output terminal of the bioelectric potential measuring means is represented as 56, and a signal generating means for generating a signal when an abnormal condition is detected is represented as 58.

Figure 6:
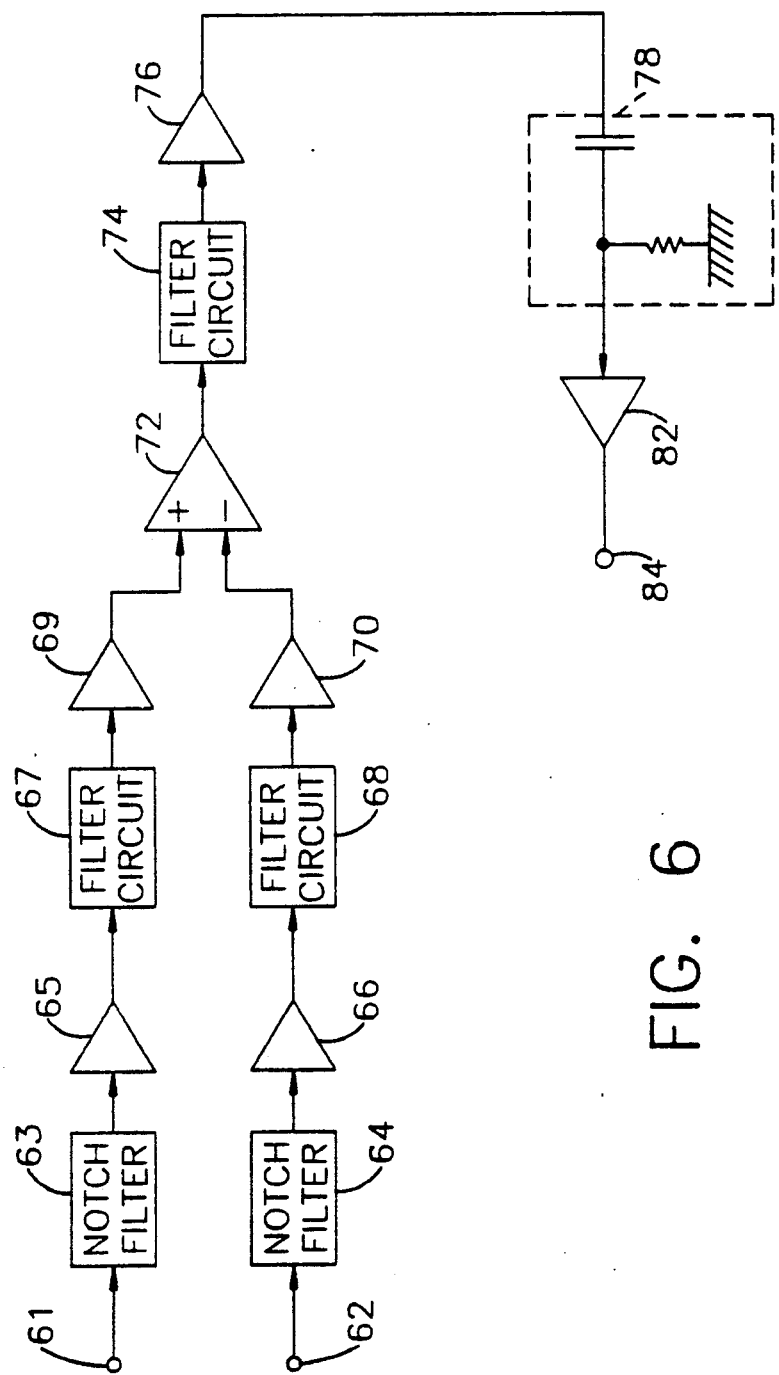

Another embodiment of the electric therapeutic apparatus of this invention is disclosed in FIGS. 6 and 7, in which the bioelectric potential measuring means having at least two electrodes for measuring the bioelectric potential independently is provided, and an output thereof is connected to the electric therapeutic apparatus.

The bioelectric potential measuring means of this embodiment has substantially the same components as shown in FIGS. 4 and 5; namely a filter circuit for substantially filtering a frequency not caused by a bioelectric potential to be detected on each of two electrodes for measuring, and an amplifier having input terminals connected to the filter circuit.

The output thereof is connected to any of the controlling means, the electric current generating means, and electrode means for the therapeutic treatment of the electric therapeutic apparatus.

As shown in FIG. 6, a desirable configuration of the bioelectric potential measuring means used in this embodiment comprises electrodes 61 and 62 for inputting a bioelectric potential, and T type notch filters 63 and 64 for filtering substantially all of the frequency caused by an electric current for the therapeutic treatment, because the current input from the electrodes includes a cyclic current caused by an electric current for the therapeutic treatment in addition to the current caused by the bioelectric potential.

Further, it comprises filter circuits 67 and 68 composed of a low pass filter or the like, buffer amplifiers 65 and 66 for matching an impedance between the filter circuits 63, 64 and the filter circuits 67, 68, a differential amplifier 72 for filtering an in-phase portion of a potential of the current wave for the therapeutic treatment and an externally induced potential, a filter circuit 74 composed of a hum filter or the like, for filtering a commercial cyclic current of 50 Hz or 60 Hz, a time constant circuit 78, an amplifier 82 including a gain adjusting means (not shown) to output the bioelectric potential, an output 84 for outputting the bioelectric potential detected, and buffer amplifiers 69, 70 and 76 for matching an impedance of the circuits existing at the front and back thereof.

The connection of the bioelectric potential measuring means to the electric therapeutic apparatus is illustrated in FIG. 7.

As shown in FIG. 7, the bioelectric potential measuring means comprises electrodes for inputting a bioelectric potential 61 and 62, filter circuits 85 and 86 which are substantially the same as the circuits shown in FIG. 6, a differential amplifier 87 for filtering an in-phase portion of a potential (carrier wave and an externally induced potential), a high cut filter 88 for cutting off a residual carrier wave, a band pass filter 89 for filtering a commercial cyclic current, an amplifier 90, and an output terminal 91 for outputting an electrocardiogram.

Further, in this embodiment, an alarm generating means 92 for comparing the detected number of an ictus cordis with a predetermined number of an ictus cordis set by an external input means (not shown) and for generating an alarm when the detected number of an ictus cordis falls outside of such a predetermined range or an irregular pulse is detected, is also provided and the output thereof is connected to the transformer 13 or the controlling means of the electric therapeutic apparatus.

EXAMPLE

Example 1

Therapeutic treatments of a total of 103 patients (42 males and 61 females) having a chronic respiratory disease and unable to expectorate sputum easily were carried out using the electric therapeutic apparatus for inducing expectoration by utilizing an interference low frequency wave (Model SK made by Minato Medical Science Co. Ltd.) which had been modified so as to output a current of up to 150 Hz to comply with the embodiment of this invention.

The treatments were carried out in such a way that vacuum pad electrodes provided with a sponge pad having an intermediate level suction force were applied to the chest and back of the patients, and the frequency applied for the therapeutic treatment were varied in four steps, e.g. 50, 70, 100, and 150 Hz, for 10 minutes during the treatment.

The patients were classified as follows:

56 examples of chronic bronchitis, 19 examples of bronchial asthma, 11 examples of bronchiolists, and 7 examples of pulmonary emphysema.

The results of the experiment are shown in Table 1 and Table 2.

As shown in the Tables, 11 examples (10.7%) showed results of "remarkably improved" (improvement of expectoration ability is more than 2 steps), 29 examples (28.1%) showed results of "improved" (improvement of the expectoration ability is more than 1 step) and 40 examples (38.9%) showed results of "slightly improved" (improvement of the expectoration ability did not reach 1 step but other symptoms were alleviated).

Accordingly, the total level of the improvements was 77.7%, which means that this kind of therapeutic treatment shows a good effect for inducing an expectoration.

TABLE 1

| General Improvement | Frequency of Interference Low Frequency Wave (Hz) | | | | TOTAL |
|---|---|---|---|---|---|
| | 50 | 70 | 100 | 150 | |
| 1. Remarkably Improved | 6 | 4 | 1 | 0 | 11 (10.7) |
| 2. Improved | 5 | 13 | 6 | 5 | 29 (38.8) |
| 3. Slightly Improved | 10 | 7 | 12 | 11 | 40 (77.7) |
| 4. Unchanged | 6 | 1 | 7 | 9 | 23 |
| 5. Aggravated | 0 | 0 | 0 | 0 | 0 |
| TOTAL | 27 | 25 | 26 | 25 | 103 |

( ) represents cumulative ratio %

TABLE 2

| Frequency (Hz) | General Improvement (cumulative %) | | | Impression of Patients |
|---|---|---|---|---|
| | Remarkably Improved | Improved | Slightly Improved | |
| 30 | — | — | — | — hard |
| 50 | 22 | 41 | 78 | AA ↑ |
| 70 | 16 | 68 | 96 | AA |
| 100 | 4 | 27 | 73 | A ↓ |
| 150 | 0 | 25 | 75 | A weak |

Note:
The general improvement is determined as follows: The general improvement is evaluated with reference mainly to Table 3 indicating a step of level of expectoration and to other items observed.
1. Remarkably Improved; Where an improvement of the expectoration of more than 2 steps is obtained.
2. Improved; Where an improvement of the expectoration of more than 1 step is obtained.
3. Slightly Improved; Where an improvement of the expectoration did not reach 1 step but another symptom was improved.
4. Unchanged; Where the symptom did not change.
5. Aggravated; Where the expectoration was aggravated or another symptom was aggravated.

TABLE 3

| Expectoration | 1. No Sputum. |
| | 2. Easy expectoration. |
| | 3. Slight difficulty with expectoration. |
| | 4. Difficult to expectorate. |
| | 5. Extremely difficult to expectorate. |

Impression of patients:
AA; Very good,
A; Good,

EXAMPLE 2

Therapeutic treatments of a total of 136 patients (91 males and 45 females) having a chronic respiratory disease and unable to expectorate sputum easily were carried out using the electric therapeutic apparatus for inducing expectoration utilizing an interference low frequency wave able to output 50, 70, and 100 Hz in accordance with the embodiment of this invention.

The treatments were carried out in such a way that electrodes provided with a sponge pad having an intermediate level suction force were applied to the chest and back of the patients and the frequency applied for the therapeutic treatment was 70 Hz for 10 minutes, and the electric current supplied for the treatment was varied from 3 to 24 mA. The average thereof was $13.6 \pm 2.8$ mA (standard deviation) at each treatment.

The patients were classified as follows:

29 examples of chronic bronchitis, 35 examples of bronchial asthma, 20 examples of bronchiolists, 14 examples of pulmonary emphysema, 17 examples of bronchiectasis, and 8 examples of pulmonary tuberculosis.

The results of this experiment are shown in Table 4.

As shown in the Table 13 examples (15.5%) in the I group and 2 examples (3.8%) in the II group showed results of "remarkably improved"; a total of 15 examples (11.0%), 29 examples (34.5%) in the I group and 7 examples (13.5%) in the II group showed results of "improved"; a total of 36 examples (13.5%): and 28 examples (33.3%) in the I group and 12 examples (23.1%) in the II group showed results of "slightly improved"; a total of 40 examples (29.4%).

Accordingly, the total level of remarkably improved, improved and slightly improved was 83.3% in I group and 40.4% in II group, and therefore, the final total was 66.9%, which means this kind of therapeutic treatment shows a good effect for inducing an expectoration.

Especially, this treatment had a better effect on the patients in the I group than that shown by the results of an experiment using an expectorant.

Figure 3:
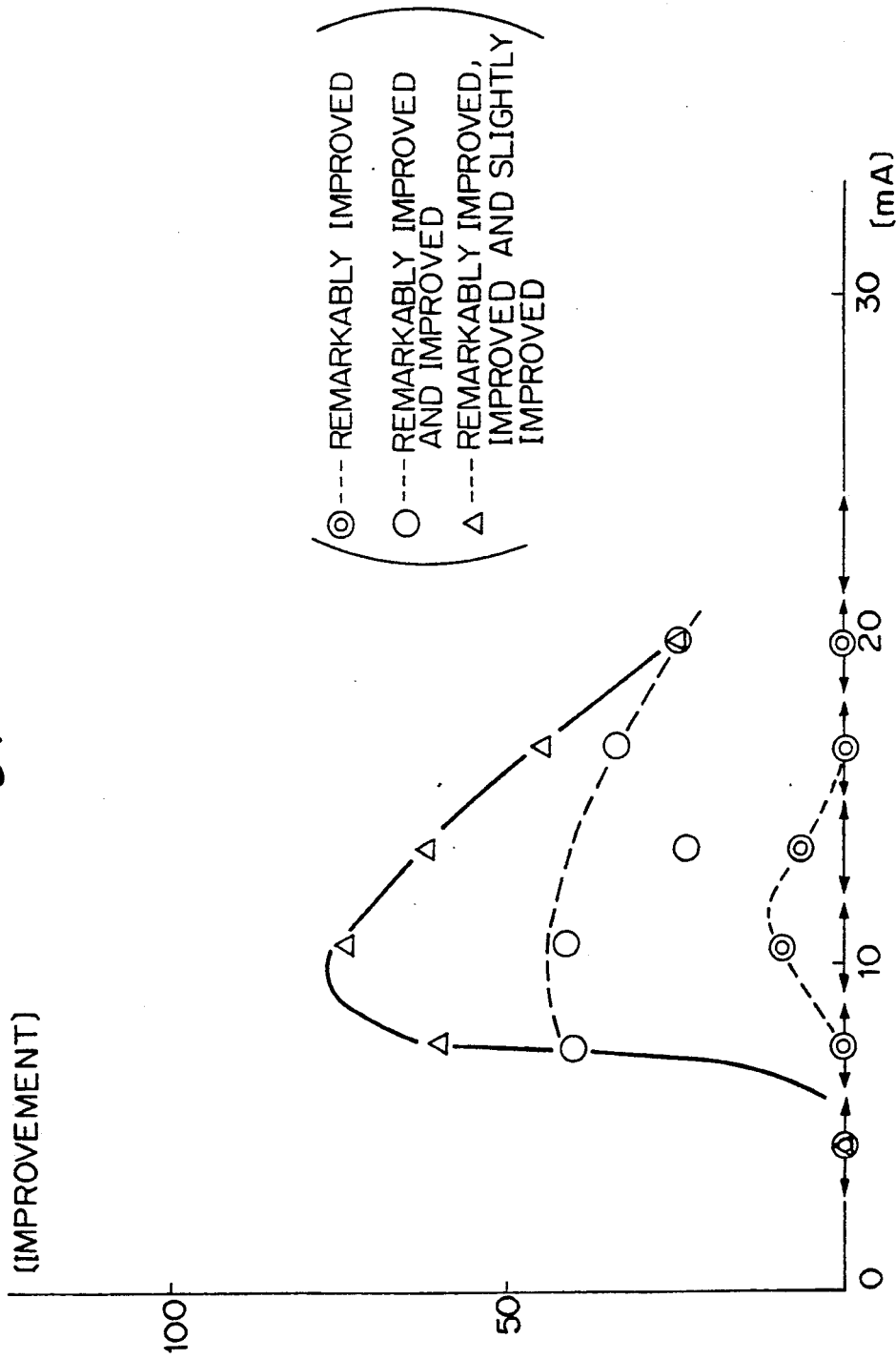
FIG. 3 is a graph indicating a relationship between a general improvement effected by and an amount of a current used for the therapy.

The relationship between an amount of current used for the treatment and the rate of improvement is shown in FIG. 3.

According to FIG. 3, it can be seen that the best effect of this invention is obtained when the current supplied is more than 6 mA.

Moreover, when the number of symptoms were fewer, the same effect was confirmed when a current of about 24 mA was supplied.

TABLE 4

| General Improvement | Disease | | |
|---|---|---|---|
| | I<br>Chronic bronchitis<br>Bronchiolitis<br>Bronchial asthma | II<br>Bronchiectasis<br>Pulmonary tuberculosis<br>Pulmonary emphysema etc. | TOTAL |
| 1. Remarkably Improved | 13 (15.5) | 2 (3.8) | 15 (11.0) |
| 2. Improved | 29 (50.0) | 7 (17.3) | 36 (37.5) |
| 3. Slightly Improved | 28 (83.3) | 12 (40.4) | 40 (66.9) |
| 4. unchanged | 14 | 31 | 45 |
| 5. Aggravated | 0 | 0 | 0 |
| TOTAL | 84 | 52 | 136 |

( ) represents a cumulative ratio %

Next, the means of fixing the electrodes used in this invention for the therapeutic treatment of a human body will be explained.

Heretofore, the electrode has been usually attached to the front of the chest area, the back of the chest area or the back of the abdomenal area of a human body by using a vacuum force or an adhesive, or by a suitable fixing device used in an electric or magnetic clinic treatment.

But however, when an electrode utilizing a vacuum force is used, the skin of the patient is deeply marked after removal of the electrodes, which makes the patient uncomfortable, and when the suction force is strong, the patient usually feels pain during the treatment. On the other hand, when an electrode is fixed with an adhesive, the patients feel a prickling sensation on the skin and the adhesive will cause a skin complaint when used several times.

It is very difficult to apply a fixing device to a human body because of variations in the proportions of the patients, and thus an improvement of such a device is desired.

Accordingly, this invention provides a suitable electrode and a device for fixing same to a human body during a therapeutic treatment.

More particularly, this invention provides an electrode and a fixing method in which a plurality of the electrodes can be easily applied and fixed to predetermined portions, such as a main portion of a human body such as the back of the chest area and the back of an abdominal area and to various limbs when necessary. Namely, they can be adjusted to be fixed to any portion of a patient in correspondence with the proportions of the patient.

According to the invention, a device for fixing an electrode to a human body basically comprises an elastic arcuate frame having a receiving portion for receiving the electrode on both ends thereof and at least one supporting member supporting the electrode and supported on the receiving portion.

Figure 8:
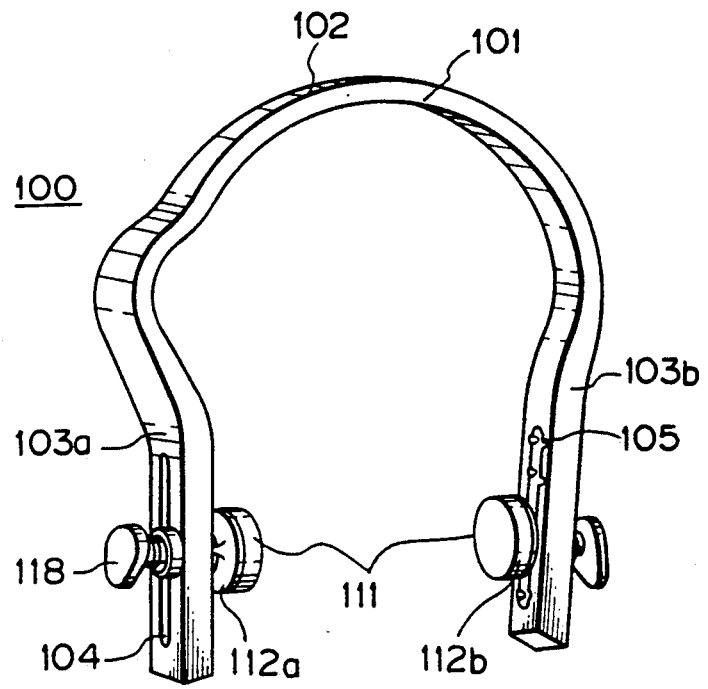
FIG. 8 shows one preferred embodiment of a fixing device for fixing an electrode used with the apparatus of this invention to a portion of a human body.

An embodiment of this invention is shown in FIG. 8.

As shown in FIG. 8, the fixing device 100 comprises an elastic arcuate frame 101, two receiving portions 103a and 103b having a slot 104 provided on both ends of the frame 101, and two supporting members 112a and 112b, each of which supports an electrode 111 and has a stem 115 inserted in the slot 104 in the receiving portions 103a and 103b respectively.

Further, a plurality of grooves 105 may be provided on an inner surface of the slot 104 for fixing an electrode more tightly, as described later.

Figure 9:
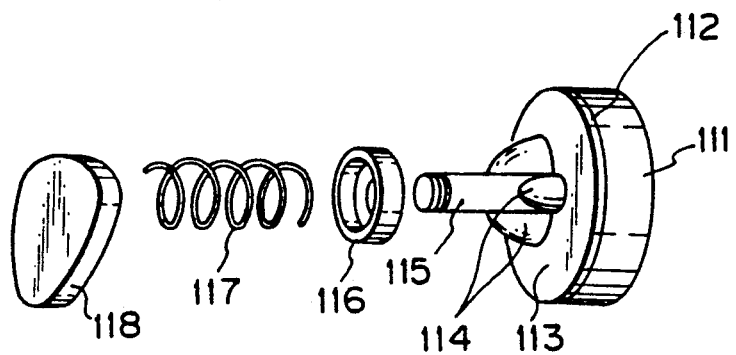
FIG. 9 shows an electrode supporting member used with the device shown in FIG. 8.

FIG. 9 shows an embodiment of the supporting member used in this invention.

As shown in FIG. 9, the supporting member 112 comprises a flat plate 113, a stem 115, a projecting portion 114 provided on a root portion of the stem 115 and adapted to be coupled to the groove 105 of the slot 104 of the receiving portion 103a or 103b, and an end portion 118 for adjusting the supporting member 112.

Further, a ring 116 and an elastic material, for example, a spring 117, may be provided between the end portion 118 and the supporting plate 113, to fixedly couple the projecting portion 114 with the groove 105.

Preferably, in practice, at least two pairs of the projecting portions 114 having different sizes are provided to enable the distance between the electrodes to be adjusted.

Usually, one supporting member is mounted on the receiving portion, but more than two of supporting members may be mounted thereon if necessary.

The electrode per se may be made of any material which does not give an electric or magnetic stimulation or energy to a human body.

As an electrode used in such an electric treatment, an electrode made of a sponge or a nonwoven fabric having water or moisture therein is preferably used.

Further, in an electric therapeutic apparatus, the electric current for the treatment is loaded to a human body through a plurality of electrodes fixed on the desired portion of the human body, with a necessary amount of current. Thus, the electrode of this invention is able to supply a current to the required portions safely and stably.

Figure 10:
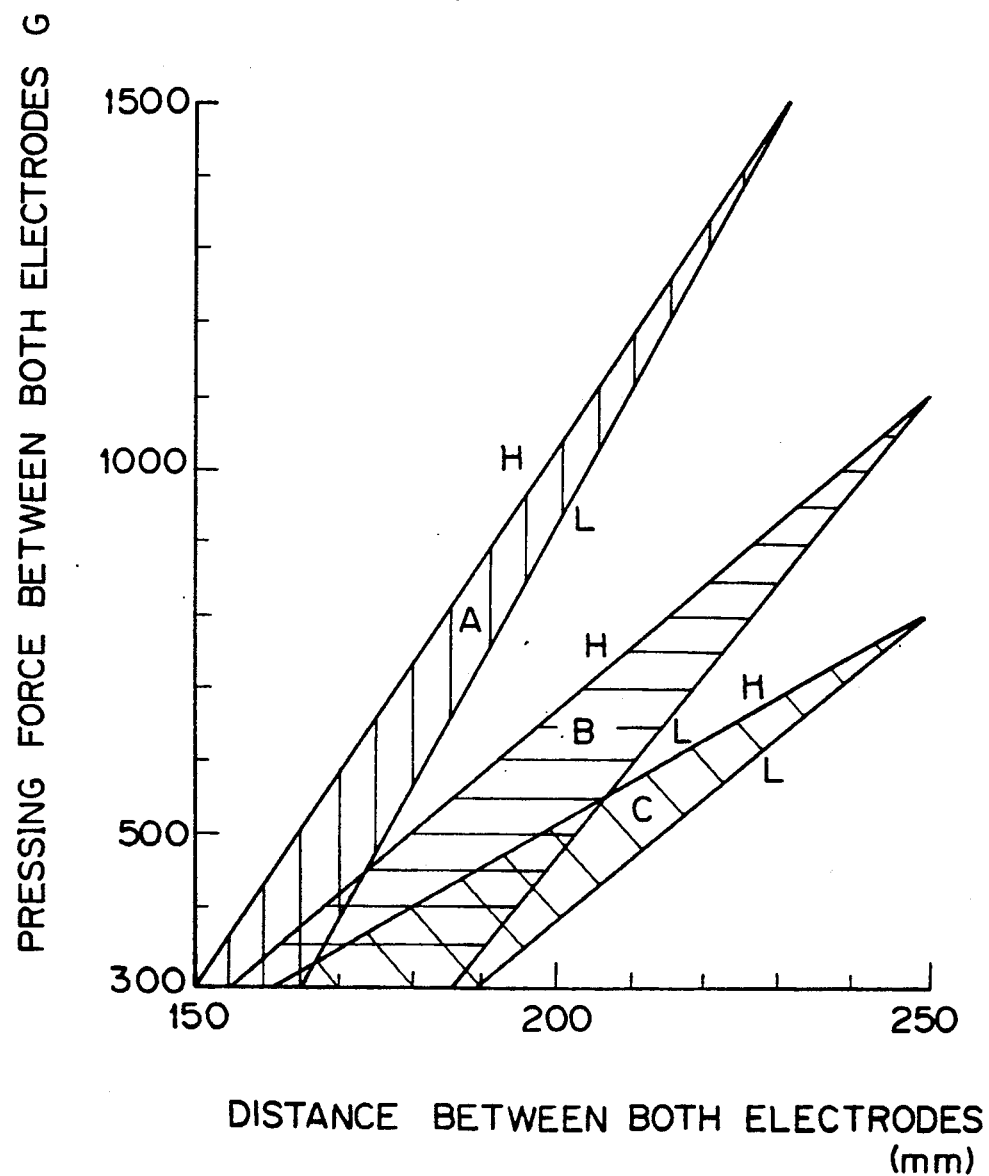
FIG. 10 is a graph indicating a relationship between a distance between both electrodes and a pressing force between both electrodes.

In FIG. 10, a relationship between a pressing force of the electrode and a distance between both electrodes, according to an example of this invention, is explained.

Namely, when the electrode is fixed to certain portion of a human body, for example, a chest portion and a back portion in this embodiment, for electric therapeutic treatment, the pressing force thereof must be at least 300 G in order to ensure a supply of a necessary current for the treatment, for example, a low frequency wave of 1 to 50 mA, stably and safely.

If this pressing force exceeds 1500 G, the fixing force is too strong, and thus the patient sometime feels uncomfortable.

Accordingly, the pressing force between both electrodes can be selected from the range of from 300 to 1500 G, depending upon the kind and size of the electrode and the portion of the human body to which the electrode is attached.

Especially, a force of from 500 G to 1200 G is most preferable for chest and back portions.

Note, the term 1 G used in this invention represents 1 g weight and denotes $1 \text{ g} \times g_0 \text{ cm/sec}^{2'}$. Wherein $g_0$ represents gravitational acceleration, the value of which is generally 980.

The fixing device of this invention can be produced by molding a metallic or plastic material.

From the viewpoints of fabrication, molding, operationability, and health, a synthetic resin material such as polycarbonate, ABS resin, polypropylene or the like is most suitable for this invention.

The arcuate shape of the elastic arcuate frame and the material thereof will generate the pressing force between both electrodes, but there is no restriction of the selection of the design or molding process.

The supporting member is also fabricated or molded in the same manner as described above.

When an elastic material is used, a synthetic spring, a coil and a flat spring can be used as the spring in this invention, but the shape or material thereof are not restricted.

The slot 104 provided on the receiving portion 103 of the elastic arcuate frame 101, grooves 105, and projecting portions 114 of the supporting member 112 are so incorporated that a distance between both electrodes and a pressing force therebetween can be adjusted in correspondence with a difference in the proportions of a human body.

In FIG. 10, A, B, and C represent examples in which the supporting member is fixed in a groove provided on an upper portion, middle portion, and a bottom portion of the slot respectively, and H and L represent examples in which the projecting portion of the supporting member is high and low, respectively.

From these examples, it can be seen that the fixing device 100 of this invention can be used in a medical treatment with a wide selection of combinations in which the distance between both electrodes can be selected from the range of 150 to 250 mm and the pressing force thereof can be selected from the range of 300 to 2500 G, more preferably from the range of 500 to 1500 G.

Another fixing device of an electrode of this invention will now be described.

This embodiment provides a fixing device whereby the position of the electrodes can be more easily adjusted.

This fixing device is characterized in that it comprises an electrode provided with a projecting portion on a surface opposite to the surface of a portion of a human being to which the electrode is attached, and a fixing belt having a plurality of openings comprising an aperture and a slit through which the projecting portion of the electrode can be penetrated.

As mentioned above, in this embodiment, an elastic belt for fixing a plurality of electrodes fixed therein and an electrode having a projecting portion on one side of the electrode opposite to the side on a human body to which it is attached are used in combination.

In this embodiment, a plurality of openings such as an aperture or a slit through which the projecting portion of the electrode can be penetrated are provided in the belt, and several groups having such a plurality of openings are provided on the belt for each electrode.

Figure 11:
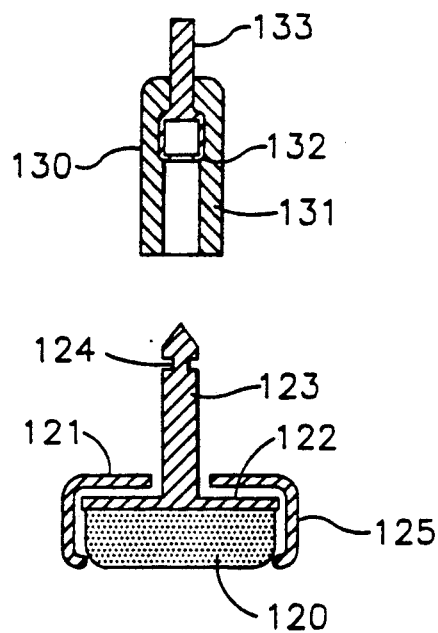
FIG. 11 is a cross sectional view of another electrode used with a fixing belt in this invention.

FIG. 11 shows the electrode used in this embodiment, wherein the electrode 121 comprises a bottom electrode plate 122 made of a metal, a projecting portion 123 mounted on one surface of the plate 122 at a right angle and an intervening material, for example a sponge 124 containing water.

Also, a pocket made of, for example, an elastomeric polymer, for enveloping the electrode, may be provided.

The coupling member 130 for the electrode comprises a cover portion 131, a stopper portion 132, a lead wire for the electrode, and a terminal 133.

As shown in FIG. 11, preferably a groove 124 is provided at the near end portion of the projecting portion, and is coupled with the projecting portion inside of the coupling member 130 to act as a stopper.

Figure 12:
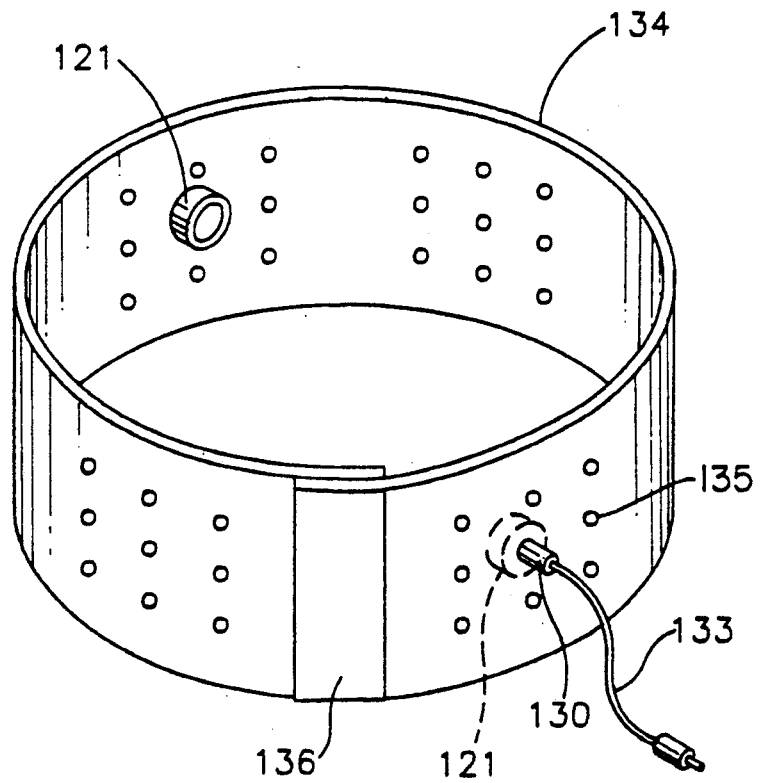
FIG. 12 is a perspective view of one embodiment of a fixing belt as a fixing device of this invention.

The elastic belt of this embodiment is illustrated in FIG. 12.

As shown, a plurality of holes are provided on the belt 134 and the belt is made of an elastic and flexible material using an elastic yarn, for example, "Spundex", elastomer materials, and a knitted fabric, and preferably, the edge of the belt and the inner peripheral portion of the holes are trimmed.

A connecting means 136, for example, buttons, hooks, fasteners, and sensitive adhesive tape or the like is provided at both ends of the belt to enable the connecting portion to be removed.

In this invention, the electrode can be attached in the desired holes corresponding to a portion of the patient to be treated, depending upon the body proportions of the patient, by inserting the projecting portion of the electrode into the hole or slit or an aperture or the like, and then coupling the projecting portion with the coupling member 130.

Figure 13:
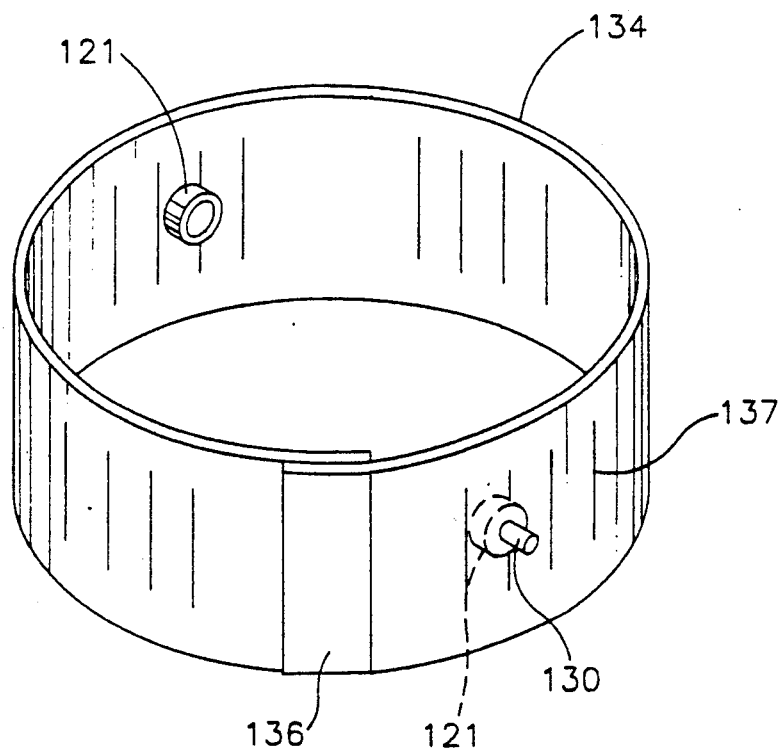
FIG. 13 and FIG. 14 are perspective views of another embodiment of a fixing belt; and, FIG. 15 and FIG. 16 are perspective views of other embodiments of a fixing device of an electrode of this invention.
Figure 14:
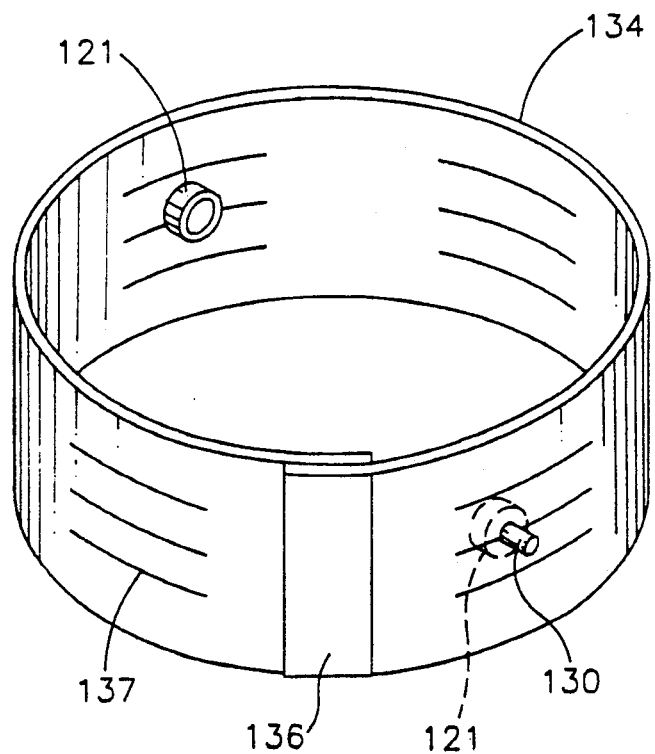

FIG. 13 shows a belt having vertical slits and FIG. 14 shows a belt having transverse slits.

Figure 15:
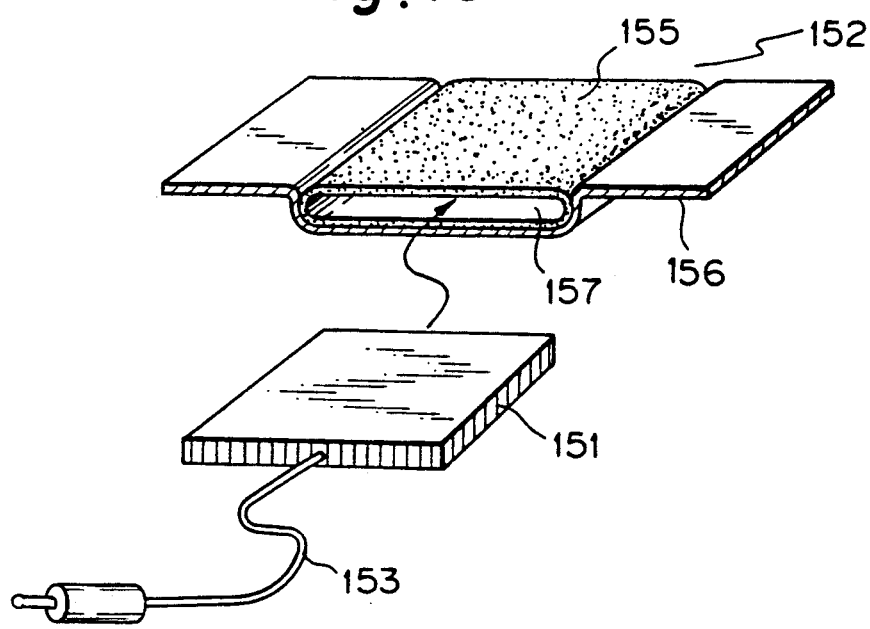

Next, another embodiment of the fixing device used in this invention will be explained. This embodiment comprised an electrode for therapeutic treatment, a connecting wire means for connecting the electrode to the therapeutic apparatus, a water-containing pocket means for storing at least a portion of the electrode therein, and a fixing belt means for fixing the pocket means, as shown in FIG. 15.

Heretofore, an electrode means combining an electrode made of a metallic plate and a water-containing sponge layer is already known, as is an adhesive electrode means comprising an electrode made of a conductive rubber material and a conductive gel or a conductive adhesive layer.

However, when the electrode is made of a sponge, a fixing device such as a belt device, or a suction device or the like for fixing the electrode to a human body is required, and these are usually complicated in structure. In addition, the electric resistance of the water-containing sponge is as large as from 300 to 1000 $\Omega/(10-15\ cm^2$ of electrode) and therefore, it is a difficult to obtain a necessary current for the therapeutic treatment, and a voltage which is about 2 or 3 times that of a necessary voltage must be loaded when a human body has a resistance of about 1000 $\Omega$.

On the other hand, an adhesive electrode has a good operational ability, but when used repeatedly, it becomes contaminated and the conductivity thereof will be reduced and, further, when used in an unrestricted manner, the patient usually feels uncomfortable.

The object of this embodiment is to provide an electrode for an electric therapeutic treatment having a low resistance and being disposable, and further, being easily attached or fixed to a human body.

According to this embodiment, an electrode consisting of a conductive element may be made of a metallic plate, a conductive rubber or a conductive elastomer. On the other hand, at least the portion which is to be attached to a portion of a human body, or preferably a whole of a water-containing pocket means, may be made of a nonwoven fabric, paper, woven fabric, thin sponge sheet or the like made of a cellulose or a hydrophilic high molecular compound which can contain water therein.

The electrode thus produced with the material mentioned above preferably has a low electric resistance of about 10-100 $\Omega/(10-15\ cm^2$ electrode).

Preferably, all portions of the water-containing pocket are made of a water-retainable material, because it is easily produced, and a predetermined amount of water can be retained therein even when a very thin material is used, and further, a good conductivity is obtained for a long time.

The water-containing pocket means 152 has an opening 157 at at least one end thereof, and thus the electrode 151 can be removably inserted into the pocket means 152.

On the other hand, as a fixing belt for fixing an electrode and the pocket means to a portion to be treated, a surgical tape, an adhesive tape such a sticking plaster or a belt such as a tape or band or the like having flexibility and stretchability can be used.

As shown in FIG. 15, an electrode 151 made of a conductive elastomer material having a rectangular shape has a lead wire 153, and a fixing device comprises a water-containing pocket means 152 made of a nonwoven fabric of cellulose 155 and a fixing belt 156 made of an adhesive tape.

In this embodiment, in the pocket means is wetted by water or moisture and used for the treatment with an electrode therein, and after the treatment, the pocket means is thrown away.

Figure 16:
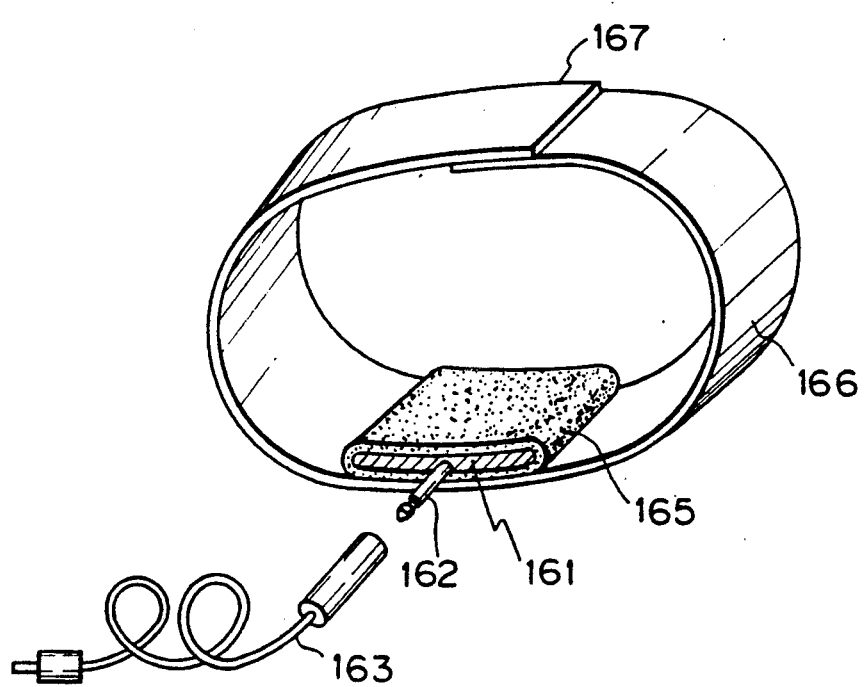

FIG. 16, shows another embodiment of a fixing device of this invention. In this embodiment, the fixing device comprises, an electrode 161 made of a metal having a terminal 162, able to be connected to a lead wire 163, a water-containing pocket means 165 made of a sponge made of a polyvinyl alcohol, and a fixing belt 166 made of a stretchable band having the same width as that of the electrode and connected at both ends thereof by a connecting means 167.

EFFECT OF THE INVENTION

As mentioned above, especially in the examples, the use of the electric therapeutic apparatus for inducing expectoration shows at least the same effect as when an expectorant is used. Further, alleviation of a cough and a reduction of fatigue of a respiratory muscle may be obtained as secondary effects.

Namely, the therapeutic apparatus of this invention induces an expectoration by a patient having difficulty therewith due to a chronic respiratory disease, and thereby greatly contributes to medical treatments and the medical industry.

Moreover, according to this invention, a bioelectric potential can be measured during the electric therapeutic treatment, and therefore, the electric therapeutic treatment can be performed while simultaneously checking a condition of a patient, and thus an electric therapeutic treatment with a high safety factor can be obtained.

Especially, since a bioelectric potential measuring means detects abnormal data and feeds it back to the electric therapeutic apparatus to stop or to reduce an electric current supply, a higher safety is maintained regardless of the supply of a current to a patient, and the total effect of the treatment is increased.

In addition to the above effects, by using a fixing device for attaching electrodes to a portion of a human body, a plurality of the electrodes for the treatment can be easily fixed to any portion of a human body, whether a predetermined portion or voluntary portion, and regardless of the differences in body proportions of patients or the medical treatment conditions.

Also a disposable electrode can be obtained.

We claim:

1. A device for fixedly applying an electrode to a portion of a human body used in an electric therapeutic treatment comprising an elastic arcuate frame having a receiving portion on both ends thereof, electrode means for establishing electrical contact with a human body, said electrode means being received in said receiving portion of said frame, at least one supporting member supporting the electrode means on a surface thereof, and a longitudinal slot provided in said receiving portion, into which at least a portion of said supporting member of said electrode means is inserted, said slot having an inner surface having a plurality of grooves therein, and said supporting member comprising a flat plate which supports the electrode means, a stem provided on a surface of the plate opposite to a surface on which the electrode means is provided and at least one projecting portion provided at a root portion of the stem which is coupled to one of said grooves provided in said slot.

2. A device according to claim 1, wherein the supporting member further comprises an end portion for transferring the supporting member by releasing the coupling between said projecting portion of the supporting member and said groove in the slot.

3. A device according to claim 2, wherein a resilient element for fixedly coupling the projecting portion with the groove is provided between said plate and said end portion.

4. A device according to claim 1, wherein said electrode means is capable of exerting a pressing force on a human body from 300 to 2500 G.

5. An electric therapeutic apparatus used for inducing expectoration comprising an electric current generating means which generates two respective carrier wave currents having an intermediate frequency different from each other, a differential frequency thereof being from 30 Hz to 150 Hz, an electric current detecting means for detecting an electric current when an electric power is supplied, an electric current controlling means for controlling the current in such a way that at least 6 mA of current flows in the apparatus when an electric power is supplied and two pairs of electrode means for establishing electrical contact with a human body consisting of at least two electrodes which provide end portions of each electrode means, said electrodes being capable of being attached to a portion of the human body in such a way that one of said electrodes of each pair of the electrode means are fixed to a chest portion of a human body and one of the other electrodes of each pair of the electrode means is fixed on a back portion thereof, so that electric current path between the electrodes of the one pair of the electrode means crosses electric current path between the electrodes of the other pair, and said apparatus further comprises a device for fixedly applying at least one of said electrode means to a portion of a human body comprising an elastic arcuate frame having a receiving portion for receiving said electrode means on both ends thereof, at least one supporting member supporting the electrode means on said receiving portion, and a longitudinal slot provided in said receiving portion, into which at least a portion of said supporting member is inserted, said slot having an inner surface having a plurality of grooves therein, and said supporting member comprising a flat plate which supports the electrode means, a stem provided on a surface of the plate opposite to a surface on which the electrode means is provided and at least one projecting portion provided at a root portion of the stem which is coupled to one of said grooves provided in said slot.

6. A device according to claim 2, wherein the supporting member further comprises an end portion for transferring the supporting member by releasing the coupling between said projecting portion of the supporting member and said groove in the slot.

7. A device according to claim 6, wherein an elastic element for fixedly coupling the projecting portion with the groove is provided between said plate and said end portion.

8. A device according to claim 7, wherein said pairs of electrode means are capable of exerting a pressing force from 300 to 2500 G therebetween.

9. An electric therapeutic apparatus according to claim 2, wherein the apparatus further comprises a timer means for setting a time for a supply of an electric power to the apparatus.

10. An electric therapeutic apparatus according to claim 1, wherein the electric current detecting means is provided with an excess current preventing means for setting an upper limit on the electric current supplied to the apparatus.

* * * * *

UNITED STATES PATENT AND TRADEMARK OFFICE
CERTIFICATE OF CORRECTION

PATENT NO. : 5,123,413

DATED : June 23, 1992

INVENTOR(S) : Hasegawa, et al.

It is certified that error appears in the above-identified patent and that said Letters Patent is hereby corrected as shown below:

Column 12, line 3, change "were" to --was--;

Column 20, line 17, change "2" to --5--;

line 30, change "2" to --5--;

line 34, change "1" to --5--.

Signed and Sealed this

Thirtieth Day of November, 1993

Attest:

BRUCE LEHMAN

Attesting Officer

Commissioner of Patents and Trademarks